(12) United States Patent
Sukegawa

(10) Patent No.: US 9,039,671 B2
(45) Date of Patent: May 26, 2015

(54) ABSORBENT PAD AND ABSORBENT ARTICLE

(75) Inventor: Hiroto Sukegawa, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 192 days.

(21) Appl. No.: 13/813,255

(22) PCT Filed: Jul. 29, 2011

(86) PCT No.: PCT/JP2011/067414
§ 371 (c)(1),
(2), (4) Date: Jan. 30, 2013

(87) PCT Pub. No.: WO2012/015025
PCT Pub. Date: Feb. 2, 2012

(65) Prior Publication Data
US 2013/0131622 A1 May 23, 2013

(30) Foreign Application Priority Data

Jul. 30, 2010 (JP) .................................. 2010-171276

(51) Int. Cl.
*A61F 13/15* (2006.01)
*A61F 13/56* (2006.01)
(Continued)

(52) U.S. Cl.
CPC .............. *A61F 13/565* (2013.01); *A61F 13/505* (2013.01); *A61F 13/532* (2013.01); *A61F 13/64* (2013.01); *A61F 13/51104* (2013.01); *A61F 13/514* (2013.01); *A61F 13/53* (2013.01); *A61F 13/625* (2013.01)

(58) Field of Classification Search
USPC ............. 604/389, 396, 385.01, 386, 387, 392
See application file for complete search history.

(56) References Cited

U.S. PATENT DOCUMENTS 3,441,025 A    4/1969  Ralph
5,133,707 A *  7/1992  Rogers et al. ................. 604/389
(Continued)

FOREIGN PATENT DOCUMENTS

JP    04-364845        12/1992
JP    4-364845 A1      12/1992
(Continued)

OTHER PUBLICATIONS

Supplementary European Search Report dated Dec. 3, 2013.
(Continued)

*Primary Examiner* — Jacqueline Stephens
(74) *Attorney, Agent, or Firm* — Arthur M. Reginelli; Renner, Kenner

(57) ABSTRACT

An absorbent pad and an absorbent article configured that engagement members are arranged at both corners of a ventral-side portion and a back-side portion on an outer sheet of the absorbent pad; a waist band including a belt-shaped body with hook materials and engagement portions attached to both end portions thereof, first and second ventral-side engagement portions across which the engagement members at the ventral-side portion of the absorbent pad are engaged, and first and second back-side engagement portions across which the engagement members at the back-side portion of the absorbent pad are engaged; and hook materials capable of engaging with the engagement members of the absorbent pad are attached to internal surfaces of the first and second ventral-side engagement portions and the first and second back-side engagement portions.

9 Claims, 18 Drawing Sheets

(51) Int. Cl.
*A61F 13/505* (2006.01)
*A61F 13/532* (2006.01)
*A61F 13/64* (2006.01)
*A61F 13/511* (2006.01)
*A61F 13/514* (2006.01)
*A61F 13/53* (2006.01)
*A61F 13/62* (2006.01)

(56) References Cited

U.S. PATENT DOCUMENTS

| | | | |
|---|---|---|---|
| 5,275,588 A * | 1/1994 | Matsumoto et al. | 604/372 |
| 5,304,162 A | 4/1994 | Kuen | |
| 5,445,628 A | 8/1995 | Gipson et al. | |
| 5,476,702 A | 12/1995 | Datta | |
| 6,045,543 A * | 4/2000 | Pozniak et al. | 604/385.01 |
| 6,334,858 B1 | 1/2002 | Ronnberg et al. | |
| 6,733,483 B2 * | 5/2004 | Raufman et al. | 604/385.01 |
| 7,211,072 B2 | 5/2007 | Nawata et al. | |
| 2005/0148980 A1 | 7/2005 | Fitton | |
| 2009/0105862 A1 | 4/2009 | Olarte | |

FOREIGN PATENT DOCUMENTS

| | | |
|---|---|---|
| JP | 11-019129 | 1/1999 |
| JP | 2000-051273 | 2/2000 |
| JP | 2003-175066 | 6/2003 |
| JP | 2005-021196 | 1/2005 |
| JP | 2010-082139 | 4/2010 |
| WO | WO200635011 A1 | 12/2006 |
| WO | PCT/IB2007/052148 | 12/2007 |
| WO | WO 2007/141750 A1 | 12/2007 |

OTHER PUBLICATIONS

International Search Report for PCT/JP2011/067414 dated Aug. 23, 2011.

* cited by examiner

ABSORBENT PAD AND ABSORBENT ARTICLE

TECHNICAL FIELD

This application is the national-stage application of International Application Serial No. PCT/JP2011/067414, filed on Jul. 29, 2011, which claims the benefit of Japanese Patent Application Serial No. JP2010-171276, filed on Jul. 30, 2010, which are incorporated herein by reference. The present invention relates to an absorbent pad and an absorbent article, more specifically to an absorbent pad and an absorbent article that can be easily replaced from the back side of a wearer.

BACKGROUND ART

Patent Literature 1 discloses a waist band including a belt-shaped body with a contractive section and a non-contractive section, a hook material attached to one peripheral end of the belt-shaped body, and an engagement section attached to the other peripheral end of the belt-shaped body, and discloses means for fixing both peripheral ends of an absorbent main body in a detachable manner to the non-contractive section on an internal surface of the waist band while a wearer is in the decubitus position.

Patent Literature 2 discloses a waist band having a detachable joint structure in which a hook material and a loop material are attached to ends of a waist sheet with waist-around resilient and elastic members sandwiched therein, and discloses means for fixing both peripheral ends of an absorbent main body in a detachable manner to an internal surface of the waist band while a wearer is in the decubitus position.

Patent Literature 3 discloses a waist band that is shaped in a circle by joining together a back-side band and a ventral-side band at both ends thereof, and discloses means for fixing a back-side end of an absorbent main body to an internal surface of the back-side band and fixing a ventral-side end of the absorbent main body to an external surface of the ventral-side band, in a detachable manner, while a wearer is in standing position.

Patent Literature 4 discloses a waist band that is shaped in a circle by joining together both ends of an outer sheet in which elastic members are arranged in the vicinity of a waist opening, and discloses means for fixing both peripheral ends of an absorbent main body in a detachable manner to an external surface of the waist band, while a wearer is in standing position.

CITATION LIST

Patent Literatures

Patent Literature 1: JP 2010-82139 A
Patent Literature 2: JP 2000-51273 A
Patent Literature 3: JP 2005-21196 A
Patent Literature 4: JP 4116285 B2

SUMMARY OF INVENTION

Technical Problem

The waist band disclosed in Patent Literature 1 or 2 is joined at the side portions of the body of a wearer, which eliminates the need to change the body position of a wearer. This provides an advantage of reducing a workload of a nursing care assistant in charge of replacing an absorbent main body on a wearer who cannot freely move his/her joints or easily change his/her body position due to rigidity.

If the waist band disclosed in Patent Document 3 or 4 is used by a wearer who can freely move his/her joints and change his/her body positions, the legs of the wearer are passed into the waist band to fix the waist band at the waist, and an absorbent main body can be easily fixed to the waist band. This provides an advantage of reducing workloads of a wearer and a nursing care assistant.

However, wearers generally have a sense of shame at replacement of absorbent main bodies. If a wearer feels a deep sense of shame, he/she may be unwilling to replace an absorbent main body, and may lapse into so-called rebelling against nursing care and behave violently on a nursing care assistant. Accordingly, there is a demand for a waist band that allows replacement of an absorbent main body from the back side of a wearer.

Therefore, a main object of the present invention is to provide an absorbent pad capable of being easily replaced from the back side of a wearer, and an absorbent article formed by a waist band and the absorbent pad. Another object of the present invention is to provide an absorbent pad and an absorbent article that can be easily adjusted in attachment positions on attachment to a wearer.

Solution to Problem

The present invention solving the foregoing issues is as follows:

<Invention According to Claim 1>

An absorbent pad, including: a liquid pervious top sheet; a liquid impervious back sheet; an absorbent body extending longitudinally between the liquid pervious top sheet and the liquid impervious back sheet at least from a crotch portion to a back-side portion; and an outer sheet on an external surface of the liquid impervious back sheet, wherein engagement members with indications of attachment positions are arranged at both corners of a ventral-side portion and a back-side portion on an external surface of the outer sheet.

(Operation and Effect)

In the invention according to Claim 1, the engagement members with the indications of attachment positions are arranged at the both corners of the ventral-side portion and the back-side portion on the external surface of the outer sheet of the absorbent pad. Accordingly, it is possible to easily replace the absorbent pad from the back side of a wearer and adjust attachment positions of the absorbent pad referring to the indications of the attachment positions as guides.

<Invention According to Claim 2>

The absorbent pad according to Claim 1, wherein leg-around resilient members are arranged at side flap portions of the absorbent pad, the leg-around resilient members extend longitudinally from the crotch portion to positions opposed to the engagement members at the ventral-side portion and the back-side portion of the outer sheet.

(Operation and Effect)

In the invention according to Claim 2, the leg-around resilient members extend longitudinally from the crotch portion to the positions opposed to the engagement members at the ventral-side portion and the back-side portion of the outer sheet, which makes it possible to, during use of the absorbent pad, generate a lifting force by contraction of the leg-around resilient members and keep a high fit of the absorbent pad to a wearer.

<Invention According to Claim 3>

The absorbent pad according to Claim 1 or 2, wherein temporary fastening members are arranged at end flap portions of the absorbent pad.

(Operation and Effect)

In the invention according to Claim 3, the temporary fastening members are arranged at the end flap portions of the absorbent pad. Accordingly, it is possible to allow a nursing care assistant to use freely his/her both hands to replace the absorbent pad more easily by temporarily fastening the temporary fastening members to the waist band. In addition, when the end flap portions of the absorbent pad are folded toward the liquid pervious top sheet and the temporary fastening members are temporarily fastened to the liquid pervious top sheet, it is possible to prevent leakage of urine or the like from both longitudinal end portions of the absorbent pad.

<Invention According to Claim 4>

An absorbent article having an absorbent pad and a waist band across which the absorbent pad is attached, wherein the absorbent pad includes: a liquid pervious top sheet; a liquid impervious back sheet; an absorbent body extending longitudinally between the liquid pervious top sheet and the liquid impervious back sheet at least from a crotch portion to a back-side portion; and an outer sheet on an external surface of the liquid impervious back sheet, and wherein engagement members with indications of attachment positions are arranged at both corners of a ventral-side portion and a back-side portion on an external surface of the outer sheet, the waist band includes:

a belt-shaped body having a belt-shaped nonwoven fabric and resilient members arranged in a stretched state along a periphery of the nonwoven fabric;

a hook material of a mechanical fastener that is attached to one peripheral end portion of the belt-shaped body, and an engagement portion that is attached to the other peripheral end of the belt-shaped body and is capable of engaging with the hook material;

a first ventral-side engagement portion across which the engagement members at the ventral-side portion of the absorbent pad are engaged, and a first back-side engagement portion across which the engagement members at the back-side portion of the absorbent pad are engaged, at a portion of the belt-shaped body opposed to the right iliac bone of a wearer;

a second ventral-side engagement portion across which the engagement members at the ventral-side portion of the absorbent pad are engaged, and a second back-side engagement portion across which the engagement members at the back-side portion of the absorbent pad are engaged, at a portion of the belt-shaped body opposed to the left iliac bone of a wearer, and wherein hook materials of mechanical fasteners capable of engaging with the engagement members of the absorbent pad are attached to internal surfaces of the first and second ventral-side engagement portions and the first and second back-side engagement portions, and the first and second ventral-side engagement portions and the first and second back-side engagement portions are inclined with respect to the longitudinal direction of the belt-shaped body, and extend beyond a lower waist portion opening edge of the belt-shaped body.

(Operation and Effect)

In the invention according to Claim 4, the absorbent pad has the engagement members with the indications of the attachment positions at the both corners of the ventral-side portion and the back-side portion on the external surface of the outer sheet. Accordingly, it is possible to easily replace the absorbent pad from the back side of a wearer and adjust the absorbent pad in attachment position referring to the indications of the attachment positions as guides.

The waist band includes a hook material that is attached to one peripheral end portion of the belt-shaped body, and an engagement portion that is attached to the other peripheral end of the belt-shaped body and is capable of engaging with the hook material, a first ventral-side engagement portion across which the engagement members at the ventral-side portion of the absorbent pad are engaged and a first back-side engagement portion across which the engagement members at the back-side portion of the absorbent pad are engaged, at a portion of the belt-shaped body opposed to the right iliac bone of a wearer, a second ventral-side engagement portion across which the engagement members at the ventral-side portion of the absorbent pad are engaged and a second back-side engagement portion across which the engagement members at the back-side portion of the absorbent pad are engaged, at a portion of the belt-shaped body opposed to the left iliac bone of a wearer. Accordingly, a nursing care assistant can attach the waist band to a wearer from the back side of the wearer, attach the absorbent pad to the waist band, and easily shape the waist band in a circle at the ventral-side intermediate portion of the body of the wearer.

The hook materials of mechanical fasteners capable of engaging with the external surface of the absorbent pad are attached to the internal surfaces of the first and second ventral-side engagement portions and the first and second back-side engagement portions, and the first and second ventral-side engagement portions and the first and second back-side engagement portions are inclined with respect to the longitudinal direction of the belt-shaped body, and extend beyond a lower waist portion opening edge of the belt-shaped body. Accordingly, it is possible to attach the waist band to a wearer in an easy manner so as to set the first and second ventral-side engagement portions and the first and second back-side engagement portions along the groin of the wearer. In addition, on replacement of the absorbent pad, it is possible to fit easily the absorbent pad to a wearer because the absorbent pad can be easily engaged with the first and second ventral-side engagement portions and the first and second back-side engagement portions of the waist band, and positions of engagement with the absorbent pad can be fine-adjusted.

<Invention According to Claim 5>

The absorbent pad according to Claim 4, wherein leg-around resilient members are arranged at the side flap portions of the absorbent pad, and the leg-around resilient members extend longitudinally from the crotch portion to positions opposed to the engagement members at the ventral-side portion and the back-side portion of the outer sheet.

(Operation and Effect)

In the invention according to Claim 5, the leg-around resilient members extend longitudinally from the crotch portion to positions opposed to the engagement members at the ventral-side portion and the back-side portion of the outer sheet. Accordingly, it is possible to, during use, generate a lifting force by contraction of the leg-around resilient members and maintain a high fit of the absorbent pad to a wearer.

<Invention According to Claim 6>

The absorbent article according to Claim 4 or 5, wherein temporary fastening members are arranged at the end flap portions of the absorbent pad.

(Operation and Effect)

In the invention according to Claim 6, the temporary fastening members are arranged at the end flap portions of the absorbent pad. Accordingly, it is possible to allow a nursing care assistant to use freely his/her both hands to replace the absorbent pad more easily by temporarily fastening the temporary fastening members to the waist band. In addition, when the end flap portions of the absorbent pad are folded toward the liquid pervious top sheet and the temporary fastening members are temporarily fastened to the liquid pervious top sheet, it is possible to prevent leakage of urine or the like from both longitudinal end portions of the absorbent pad.

<Invention According to Claim 7>

The absorbent article according to any one of Claims 4 to 6, wherein fixed portions of the first and second ventral-side engagement portions with the belt-shaped body are formed at a position opposed to the iliac bone of a wearer, and a shape of the fixed portions is approximate to a substantially triangular shape of the iliac bone.

(Operation and Effect)

In the invention according to Claim 7, the fixed portions of the first and second ventral-side engagement portions with the belt-shaped body are formed at a position opposed to the iliac bone of a wearer, and the shape of the fixed portions is approximate to a substantially triangular shape of the iliac bone. Accordingly, the fixed portions of the first and second ventral-side engagement portions with the belt-shaped body are positioned on a concave part over the iliac bone of a wearer to support the waist band. This eliminates the fear that the waist band slips down during use.

<Invention According to Claim 8>

The absorbent article according to any one of Claims 4 to 7, wherein an end of the first ventral-side engagement portion and an end of the second back-side engagement portion are fixed with a clockwise inclination of 30 to 60 degrees with respect to the periphery of the belt-shaped body, and an end of the second ventral-side engagement portion and an end of the first back-side engagement portion are fixed with a counterclockwise inclination of 30 to 60 degrees with respect to the periphery of the belt-shaped body.

(Operation and Effect)

In the invention according to Claim 8, an end of the first ventral-side engagement portion and an end of the second back-side engagement portion are fixed with a clockwise inclination of 30 to 60 degrees with respect to the periphery of the belt-shaped body, and an end of the second ventral-side engagement portion and an end of the first back-side engagement portion are fixed with a counterclockwise inclination of 30 to 60 degrees with respect to the periphery of the belt-shaped body. Accordingly, if the absorbent pad is attached across the waist band, a lifting force toward a wearer is generated at the absorbent pad, which makes it possible to maintain a high fit of the absorbent pad to the wearer. In addition, it is possible to attach the waist band more easily and attach the absorbent pad across the waist band more easily.

<Invention According to Claim 9>

The absorbent article according to any one of Claims 4 to 8, wherein when being stretched by 150%, a stretching stress of the resilient members arranged at the waist portion of the belt-shaped body is 10 to 35 g, and a stretching stress of the resilient members arranged at the lower waist portion of the belt-shaped body is 4 to 15 g.

(Operation and Effect)

In the invention according to Claim 9, when being stretched by 150%, a stretching stress of the resilient members arranged at the waist portion of the belt-shaped body is 10 to 35 g, and a stretching stress of the resilient members arranged at the lower waist portion is 4 to 15 g. Accordingly, the waist portion of the belt-shaped body can be firmly attached to a narrowed portion above the iliac bone of a wearer. This eliminates the fear that the waist band slips down from the attachment position during use. In addition, it is possible to prevent that the lower waist portion of the belt-shaped body overlapping the absorbent pad is excessively pressed.

<Invention According to Claim 10>

The absorbent article according to any one of Claims 4 to 9, wherein recognizable marks are provided on an external surface of an end portion and an external surface of a peripherally central portion of the belt-shaped body, such that the ventral-side central portion and the back-side central portion have the marks when the belt-shaped body is shaped in a circle, and a longitudinally extending recognizable mark is provided at the laterally central portion of the outer sheet of the absorbent pad.

(Operation and Effect)

In the invention according to Claim 10, when the belt-shaped body is shaped in a circle, the ventral-side central portion and the back-side central portion have the marks, and the outer sheet of the absorbent pad has the longitudinally extending mark, which allows a nursing care assistant to attach easily the absorbent pad to the waist band referring to the marks as guides.

<Invention According to Claim 11>

The absorbent article according to any one of Claims 4 to 10, wherein first cut-off portions are formed from end pieces of the lower waist portion at both end portions of the belt-shaped body, a second cut-off portion is formed from an end piece of the lower waist portion at an peripherally central portion of the belt-shaped body, and when the belt-shaped body is shaped in a circle, the belt-shaped body has a ventral-side cut-off portion including the pair of first cut-off portions and a ventral-side cut-off portion including the second cut-off portion.

(Operation and Effect)

In the invention according to Claim 11, when the belt-shaped body is shaped in a circle, the belt-shaped body has a ventral-side cut-off portion including the pair of first cut-off portions and a ventral-side cut-off portion including the second cut-off portion. Accordingly, it is possible to reduce the area of the liquid pervious top sheet of the absorbent pad covered by the waist band and use substantially the entire internal section of the absorbent pad as an absorbent surface.

<Invention According to Claim 12>

The absorbent article according to any one of Claims 4 to 12, wherein a first skin protection portion is provided on the internal surface of the belt-shaped body opposed to the right iliac bone of a wearer, and a second skin protection portion is provided on the internal surface of the belt-shaped body opposed to the left iliac bone of a wearer.

(Operation and Effect)

In the invention according to Claim 12, the first skin protection portion is provided on the internal surface of the belt-shaped body opposed to the right iliac bone of a wearer, and the second skin protection portion is provided on the internal surface of the belt-shaped body opposed to the left iliac bone of a wearer. Accordingly, the first and second ventral-side engagement portions and the first and second back-side engagement portions do not rub against the skin of a wearer, which eliminates the fear of causing injuries on the skin of the wearer.

Advantageous Effects of Invention

As described above, according to the present invention, it is possible to replace easily the absorbent pad and the absorbent article including the waist band and the absorbent pad from the back side of a wearer, and it is possible to, on attachment to a wearer, adjust easily the attachment positions of the absorbent pad and the absorbent article.

DESCRIPTION OF EMBODIMENTS

Figure 1:
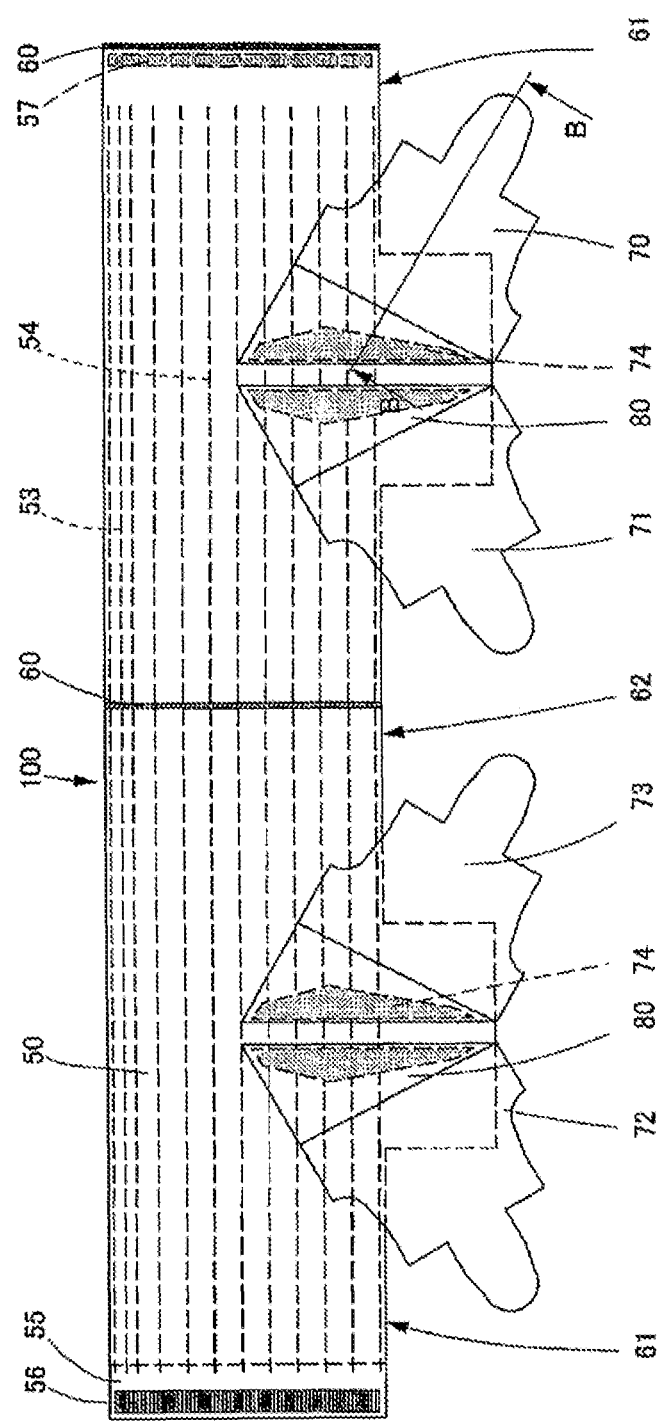
FIG. 1 is a planar view of an external surface side of a waist band in an open state.
Figure 2:
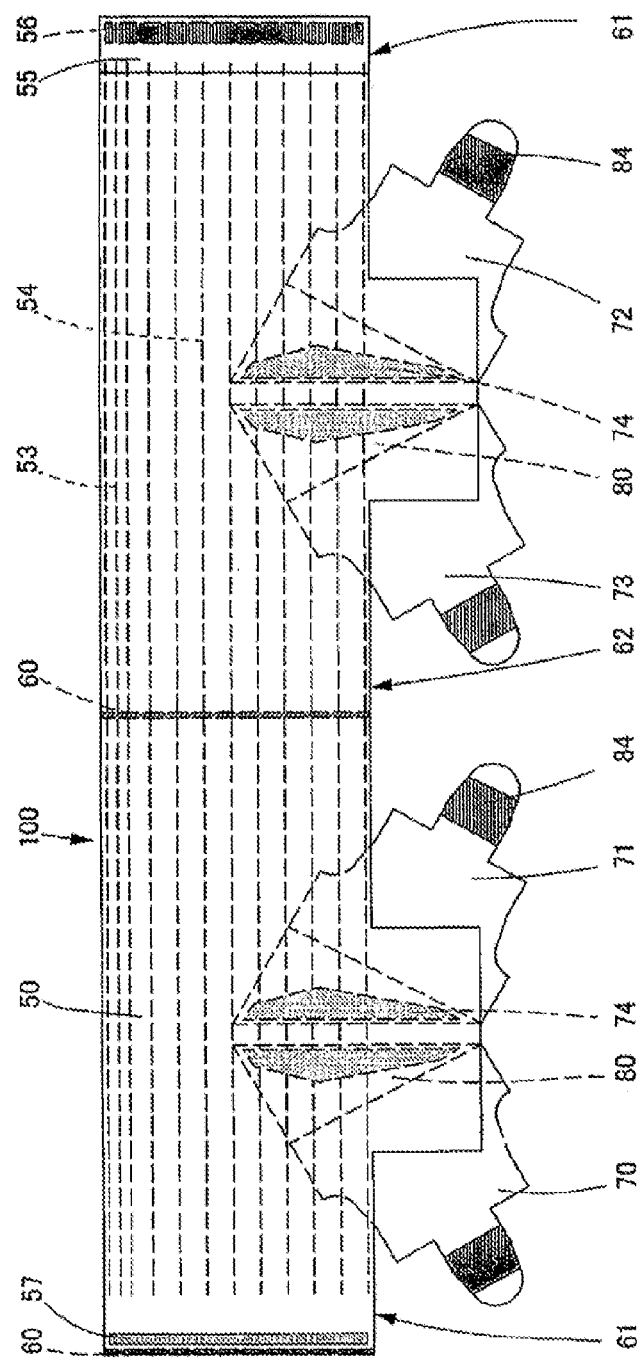
FIG. 2 is a planar view of an internal surface side of the waist band in an open state.
Figure 3:
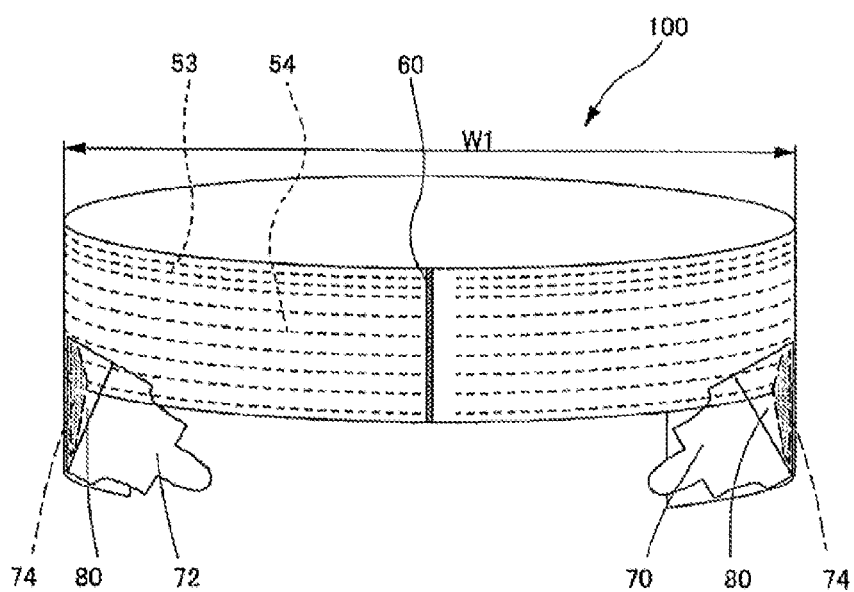
FIG. 3 is a front (ventral-side) view of the waist band shaped in a circle.
Figure 4:
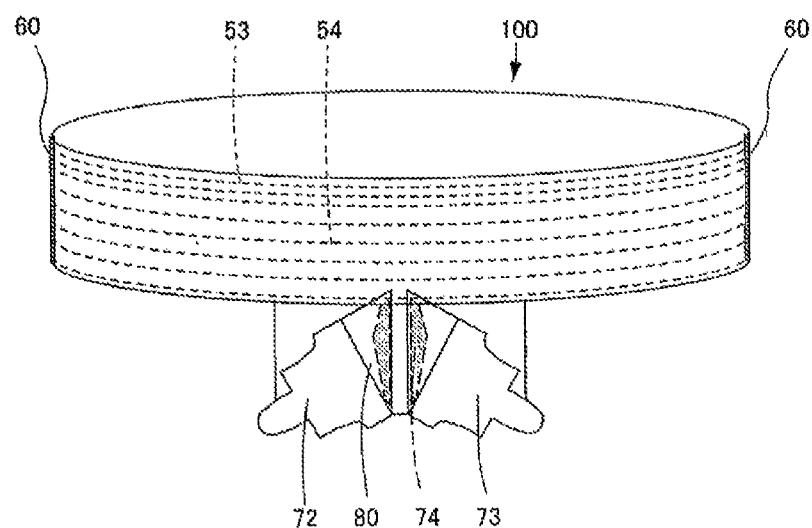
FIG. 4 is a left side view of the waist band shaped in a circle.

An embodiment of the present invention will be described with reference to the attached drawings. In the following description, the term "internal surface" refers to a surface facing the body of a wearer, and the term "external surface" refers to a surface opposite to the surface facing the body of a wearer. The term "longitudinal direction" refers to an up-down direction, and the term "peripheral direction (lateral direction)" refers to a right-left direction perpendicular to the longitudinal direction. The term "approximation" relates to not only a substantially triangular shape similar to the shape of an iliac bone but also a circular shape and an oval shape. The term "stretched by 150%" refers to, if it is assumed that resilient members have a natural length (L0) and a stretched length (L1), a value calculated by the equation "stretched length (L1)/natural length (L0) of the resilient members× 100[%]."

In addition, the term "crotch portion" refers to a portion corresponding to the crotch of a wearer, the term "ventral-side (front-side) portion" refers to a portion nearer the ventral side than the crotch portion, and the term "back-side (back-side) portion" refers to a portion nearer the back side than the crotch portion.

<Waist Band>

As shown in FIGS. 1 to 4, a waist band 100 in an embodiment of the present invention includes a belt-shaped body 50, first and second ventral-side engagement portions 70 and 72 for attachment of the ventral side of an absorbent pad 200, and first and second back-side engagement portions 71 and 73 for attachment of the back side of the absorbent pad 200.

When the waist band 100 is attached to a wearer, first, the peripherally central portion of the belt-shaped body 50 is applied to the back side of the wearer, then the waist of the wearer is surrounded by the belt-shaped body 50 while the both peripheral end portions of the belt-shaped body 50 are stretched to the right and left sides of the waist of the wearer, and finally the hook material 56 and the loop material 57 of the belt-shaped body 50 are engaged at the ventral side of the wearer to form the waist band 100 in a circle.

Although depending on the size of the waist band 100, the waist band 100 shaped in a circle has a general width W1 of 130 to 400 mm, the belt-shaped body 50 has a longitudinal length T1 of 60 to 160 mm, a waist portion W constituting a longitudinal upper portion of the belt-shaped body 50 has a longitudinal length T2 of 15 to 40 mm, and a lower waist portion U constituting a longitudinally lower portion of the belt-shaped body 50 has a longitudinal length T3 of 45 to 120 mm.

<Belt-Shaped Body>

Figure 5:
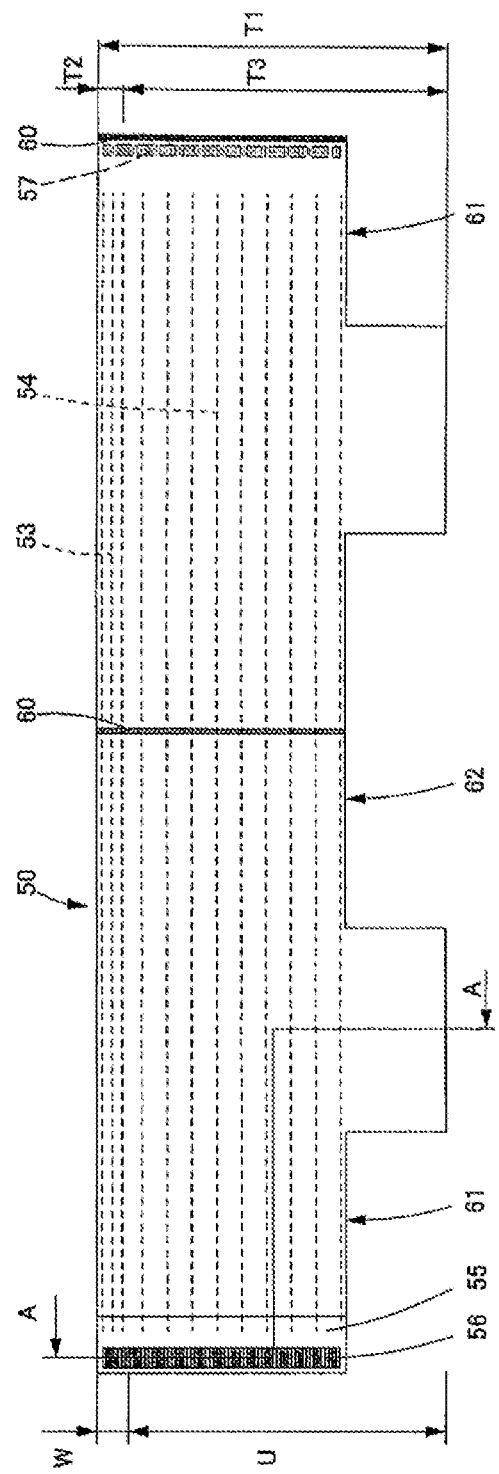
FIG. 5 is a planar view of an external surface side of a belt-shaped body in an open state.
Figure 6:
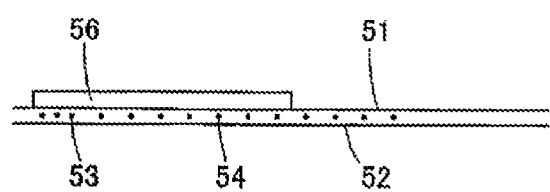
FIG. 6 is an enlarged cross section view of FIG. 5 taken along line A-A.

As shown in FIGS. 5 and 6, the belt-shaped body 50 of the waist band 100 includes an upper layer nonwoven fabric 51 forming an external surface thereof, a lower layer nonwoven fabric 52 forming an internal surface thereof, and a plurality of resilient members arranged between the upper layer nonwoven fabric 51 and the lower layer nonwoven fabric 52.

Material fibers for the upper and lower layer nonwoven fabrics 51 and 52 may be synthetic fibers based on olefin such as polyethylene or polypropylene, polyester, amide, or the like, or reproduced fibers of rayon, cupra, or the like, or natural fibers of cotton, or the like. The upper layer nonwoven fabric 51 may be a resilient plastic sheet instead of a non-woven fabric.

Four to ten waist resilient members 53 are peripherally arranged at the waist portion W of the belt-shaped body 50 at intervals of 2 to 6 mm therebetween. To attach reliably the waste portion W to the narrowed portion above the iliac bone of a wearer, the waist resilient members 53 preferably have a stretching stress of 10 to 35 g when being stretched by 150% and a fineness of 620 dtex or less.

Five to twenty lower waist resilient members 54 are peripherally arranged at the lower waist portion U of the belt-shaped body 50 at intervals of 10 to 20 m therebetween. To avoid an excessive stress on the lower waist of a wearer, the lower waist resilient members 54 preferably have a stretching stress of 4 to 15 g when being stretched by 150% and a fineness of 620 dtex or less.

To prevent separation between a hook material 56 and a loop material 57 described later and the belt-shaped body 50, the waist resilient members 53 and the lower waist resilient members 54 preferably do not extend to a portion of the belt-shaped body 50 to which the hook material 56 and the loop material 57 are provided.

In this embodiment, the waist resilient members 53 of the belt-shaped body 50 are rubber threads, but may be tape-like resilient members instead of rubber threads.

The hook material 56 of a mechanical fastener is provided via a supporting member 55 at one peripheral end of the external surface of the belt-shaped body 50, and the loop material 57 of the mechanical fastener is provided at the other peripheral end of the internal surface of the belt-shaped body.

Although depending on the size of the belt-shaped body 50, to provide a desired engagement strength, the hook material 56 is generally shaped in a rectangle with a width of 10 to 25 mm and a longitudinal length of 55 to 155 cm, and the loop material 57 is generally shaped in a rectangle with a width of 5 to 15 mm and a longitudinal length of 50 to 150 cm.

The engagement strength here refers to a strength against a shear force acting on an engagement surface between the hook material 56 and the loop material 57. To prevent separation of the engagement surface between the hook material 56 and the loop material 57 due to movements of a wearer on walking, seating or the like, in the case of a normal wearer, the hook material 56 and the loop material 57 preferably have a shear stress of 5 $N/cm^2$ or more, and have an engagement strength of 60 N or more.

The supporting member 55 may use various materials such as nonwoven fabrics, woven fabrics, net clothes, or the like. To attach the waist band 100 closely to a wearer, the supporting member 55 preferably uses a resilient nonwoven fabric that stretches in the peripheral direction. In this embodiment, a thermal bond is used to fix the hook material 56 to the external surface of the supporting member 55, and the loop material 57 to the internal surface of the belt-shaped body 50, but any other publicly-known adhesive, or an ultrasonic bond may be used instead.

To attach easily the absorbent pad 200 to the waist band 100, recognizable marks 60 are provided at the central portion of the external surface of the belt-shaped body 50 and at a peripheral end of the external surface of the belt-shaped body 50 with the loop material 57.

In addition, to use efficiently the entire area of the liquid pervious top sheet 22 of the absorbent pad 200 as a body fluid absorbent surface, first cut-off portions 61 are formed at the lower waist portion U at both peripheral ends of the belt-shaped body 50, and a second cut-off portion 62 is formed at the lower waist portion U at the peripherally central portion of the belt-shaped body 50. Accordingly, when the waist band 100 is shaped in a circle, the waist band 100 has approximately trapezoidal cut-off portions formed at the lower waist portion U on the ventral and back sides of a wearer, so that the lower waist portion U does not cover the liquid pervious top sheet 22 of the absorbent pad 200.

Further, to protect the skin of a wearer from contact with first and second ventral-side engagement portions 70 and 72 and first and second back-side engagement portions 71 and 73 described later, protection sheets (not shown) may be provided on the internal surface of the belt-shaped body 50 opposed to the first ventral-side engagement portion 70 and the first back-side engagement portion 71 and the second ventral-side engagement portion 72 and the second back-side engagement portion 73.

The protection sheets may be made of a nonwoven fabric, and material fibers for the nonwoven fabric may be synthetic fibers based on olefin such as polyethylene or polypropylene, polyester, amide, or the like, reproduced fibers of rayon, cupra or the like, or natural fibers of cotton or the like.

<Engagement Portion>

As shown in FIGS. 1 to 4, the first ventral-side engagement portion 70 is fixed to an external surface of the upper layer nonwoven fabric 51 of the belt-shaped body 50 opposed to the right iliac bone of a wearer, and the first back-side engagement portion 71 is fixed to the external surface of the upper layer nonwoven fabric 51 of the belt-shaped body 50 located more inward than the first ventral-side engagement portion 70, in a symmetrical relationship to the first ventral-side engagement portion 70.

The second ventral-side engagement portion 72 is fixed to the external surface of the upper layer nonwoven fabric 51 of the belt-shaped body 50 opposed to the left iliac bone of a wearer, and the second back-side engagement portion 73 is fixed to the external surface of the upper layer nonwoven fabric 51 of the belt-shaped body 50 located more inward than the second ventral-side engagement portion 72, in a symmetrical relationship to the second ventral-side engagement portion 72.

The first ventral-side engagement portion 70 and the second back-side engagement portion 73 are formed in the same shape, and the second ventral-side engagement portion 72 and the first back-side engagement portion 71 are formed in the same shape.

To prevent the waist band 100 from slipping down during use, fixed portions 74 of attachment sheets 80 of the first and second ventral-side engagement portions 70 and 72 are shaped in a substantially oval approximated to the right and left iliac bones of a wearer, respectively.

The fixed portions 74 for fixing the first and second ventral-side engagement portions 70 and 72 to the upper layer nonwoven fabric 51 of the belt-shaped body 50 are less stretched under influence of the waist resilient members 53 and the lower waist resilient members 54. Accordingly, when the fixed portions 74 are positioned on concave parts over the right and left iliac bones of a wearer, movement of the fixed portions 74 is restricted due to the concave parts of the body of the wearer.

Alternatively, the fixed portions 74 of the attachment sheets 80 of the first and second ventral-side engagement portions 70 and 72 may be shaped in a circle or a triangle.

To attach easily the absorbent pad 200 to the waist band 100 and maintain a favorable fit of the absorbent pad 200 to a wearer, it is preferred to fix upper pieces of the attachment sheets 80 of the first ventral-side engagement portion 70 and the second back-side engagement portion 73 to the upper layer nonwoven fabric 51 of the belt-shaped body 50 with a clockwise inclination of 30 to 60 degrees with respect to the peripheral direction, and fix upper pieces of the attachment sheets 80 of the second ventral-side engagement portion 72 and the first back-side engagement portion 71 to the upper layer nonwoven fabric 51 of the belt-shaped body 50 with a counterclockwise inclination of 30 to 60 degrees with respect to the peripheral direction.

Figure 7:
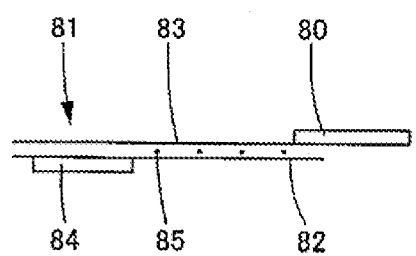
FIG. 7 is an enlarged cross section view of FIG. 1 taken along line B-B.

As shown in FIG. 7, each of the first and second ventral-side engagement portions 70 and 72 and the first and second back-side engagement portions 71 and 73 is formed by the attachment sheet 80 and a resilient sheet 81, and has a hook material 84 of a mechanical fastener attached with a thermal bond to an internal surface of a leading end portion of the resilient sheet 81.

The attachment sheet 80 may use various kinds of materials such as nonwoven fabrics, woven fabrics, knitted fabrics, or the like. The resilient sheet 81 includes an upper layer nonwoven fabric 82 forming an external surface and a lower layer nonwoven fabric 83 forming an internal surface. To attach easily the absorbent pad 200 and enhance a fit of the absorbent pad 200 to a wearer, a plurality of resilient members 85 is arranged between the upper layer nonwoven fabric 82 and the lower layer nonwoven fabric 83.

Material fibers for the upper and lower layer nonwoven fabrics 82 and 83 may be synthetic fibers based on olefin such as polyethylene or polypropylene, polyester, or amide or the like, reproduced fibers of rayon, cupra, or the like, or natural fibers of cotton or the like. Alternatively, the upper and lower layer nonwoven fabrics 82 and 83 may be resilient plastic sheets instead of nonwoven fabrics.

Figure 8:
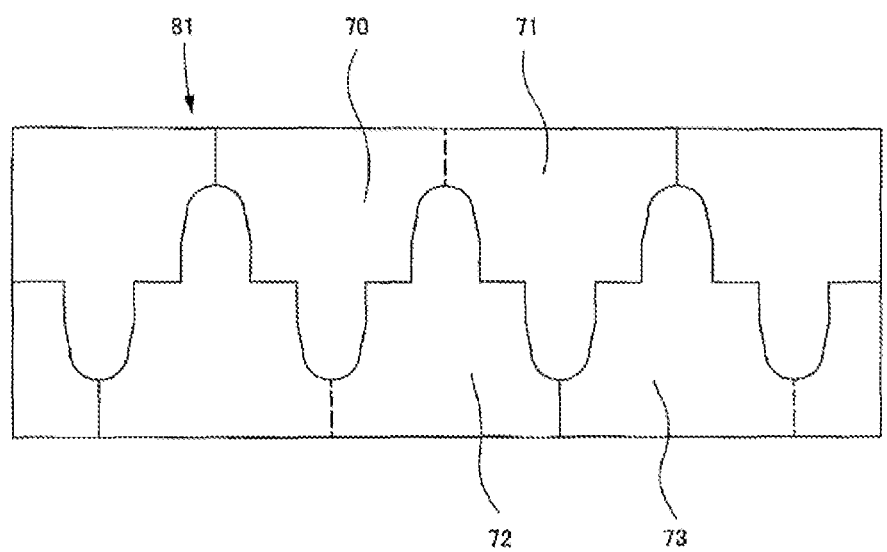
FIG. 8 is a conceptual diagram of manufacture of first and second ventral-side engagement portions and first and second back-side engagement portions.

As shown in FIG. 8, the resilient sheets 81 of the first and second ventral-side engagement portions 70 and 72 and the first and second back-side engagement portions 71 and 73 are formed in the same shape. This makes it possible to produce the resilient sheets 81 continuously from one rectangular nonwoven fabric sheet using a rotor cutter, and reduce an amount of waste of a nonwoven fabric sheet.

<Absorbent Pad>

FIGS. 9 to 16 show an example of the absorbent pad 200 according to the present invention. The absorbent pad 200 has a crotch portion C2 and a ventral-side portion F2 and a back-side portion B2 extending on both sides of the crotch portion C2 in the longitudinal direction thereof. Dimensions of the portions can be decided as appropriate. For example, an entire length of the article (longitudinal length) M may be about 350 to 700 mm, and an entire width W1 of the same may be about 130 to 400 mm (which, however, is smaller than the width of the absorbent surface of the diaper). In this case, a longitudinal length of the crotch portion C2 may be about 10 to 150 mm, a longitudinal length of the ventral-side portion F2 may be about 50 to 350 mm, and a longitudinal length of the back-side portion B2 may be about 50 to 350 mM.

The absorbent pad 200 has a basic structure in which an absorbent body 23 intervenes between an internal surface of a liquid impervious back sheet 21 having an outer sheet 32 layered on an external surface thereof and a liquid pervious top sheet 22.

The liquid impervious back sheet 21 is arranged on an underside surface of the absorbent body 23 so as to slightly extend off peripheral edges of the absorbent body 23. The liquid impervious back sheet 21 may be a polyethylene film or the like, or may be a sheet allowing moisture penetration without deteriorating a water shielding property from the viewpoint of prevention of stuffiness. The water-shielding and moisture-penetrating sheet may be a microporous sheet obtained by melting and kneading an inorganic filling agent in an olefin resin such as polyethylene, polypropylene, or the like, for example, to form a sheet and then stretching the sheet in a uniaxial or biaxial direction.

In addition, an external surface of the liquid impervious back sheet 21 is covered with the outer sheet 32 made of a nonwoven fabric. The outer sheet 32 extends off peripheral edges of the back sheet 21, by a predetermined extension width. The outer sheet 32 may use various kinds of nonwoven fabrics. Material fibers for the nonwoven fabric may be synthetic fibers based on olefin such as polyethylene or polypropylene, polyester, amide, or the like, reproduced fibers of rayon, cupra, or the like, or natural fibers of cotton or the like.

Fixed with a thermal bond to both corners of the ventral-side portion F2 and the back-side portion B2 of the outer sheet 32 are engagement members 93 formed by loop members engaging with the hook materials 84 of the first and second ventral-side engagement portions 70 and 72 and the first and second back-side engagement portions 71 and 73 of the waist band 100. Recognizable marks 60 are provided on the peripherally central portion and the longitudinally central portion of the outer sheet 32.

To attach easily the absorbent pad 200 to the waist band 100, the engagement members 93 are preferably fixed to the outer sheet 32 according to the inclination angles of the first and second ventral-side engagement portions 70 and 72 and the first and second back-side engagement portions 71 and 73 of the waist band 100. To prevent separation of the engagement surface between the hook material 84 and the engagement member 93 due to movements of a wearer on walking, seating or the like, in the case of a normal wearer, the hook material 84 and the engagement member 93 preferably have a shear stress of 5 N/cm$^2$ or more, and have an engagement strength of 60 N or more.

The face side of the absorbent body 23 is covered with the liquid pervious top sheet 22. In the illustrated mode, the absorbent body 23 partially extends off side edges of the top sheet 22. Alternatively, the top sheet 22 may be widened such that the side edges of the absorbent body 23 do not extend off. The top sheet 22 may be a porous or nonporous nonwoven fabric, or a perforated plastic sheet, or the like. Material fibers for the nonwoven fabric may be synthetic fibers based on olefin such as polyethylene or polypropylene, polyester, amide, or the like, reproduced fibers of rayon, cupra, or the like, or natural fibers of cotton or the like.

An interlayer sheet 25 desirably intervenes between the top sheet 22 and the absorbent body 23. The interlayer sheet 25 is provided to prevent a backflow of urine absorbed by the absorbent body 23, and desirably uses a material with a low water retention property and a high liquid pervious property, for example, a mesh film or the like. If it is assumed that a front end of the top sheet 22 is located at a position of 0% and a back end of the top sheet 22 is located at a position of 100%, the front end of the interlayer sheet 25 is preferably positioned within a range of 0 to 11%, and the back end of the interlayer sheet 25 is preferably positioned within a range of 92 to 100%. In addition, a width 25w of the interlayer sheet 25 is preferably about 50 to 90% of a width L2 of an upper layer absorbent body 23U described later.

At both longitudinal end portions of the absorbent pad 200, the outer sheet 32 and the liquid pervious top sheet 22 are extended and adhered to each other on both sides of the ventral-side and back-side ends of the absorbent body 23 in the longitudinal direction thereof, thereby to form end flap portions EF without the absorbent body 23.

To prevent leakage of absorbed urine from the both longitudinal end portions of the absorbent pad 200, leakage prevention sheets 91 are provided at the end flap portions EF, and temporary fastening members 92 formed by loop members are fixed with a thermal bond to external surfaces of the leakage prevention sheets 91.

The leakage prevention sheets 91 may use a material such as a plastic sheet or a melt-blown nonwoven fabric, but preferably use a nonwoven fabric made water-repellent using silicon or the like, from the viewpoint of texture.

The temporary fastening members 92 may be provided to the end flap portions EF without the leakage prevention sheets 91. In this case, it is possible to prevent leakage of absorbed urine from the both longitudinal end portions of the absorbent pad 200 by folding the end flap portions EF toward the liquid pervious top sheet 22 and then temporarily fastening the temporary fastening members 92 to the liquid pervious top sheet 22.

At the both side portions of the absorbent pad 200, the outer sheet 32 extends more outside than the side edges of the absorbent body 23, and barrier sheets 24 are entirely longitudinally adhered at laterally outside portions 24x to the entire internal surface of the absorbent pad 200 ranging from the extension portions to the side portions of the top sheet 22, thereby forming side flap portions SF without the absorbent body 23. The adhered portions are shown in a dotted-line pattern in FIG. 9, and can be formed with a hot-melt adhesive, a heat seal, or an ultrasonic seal. The end flap portions EF and the side flap portions SF constitute the peripheral edges of the present invention, and a portion surrounded by the peripheral edges constitutes a main unit section of the present invention. If the outer sheet 32 is not provided, the liquid impervious back sheet 21 may be extended to the side flap portions SF instead of the outer sheet 32, thereby forming the external surface sides of the side flap portions SF.

The barrier sheet 24 may use a material such as a plastic sheet or a melt-blown nonwoven fabric, and preferably uses a nonwoven fabric made water-repellent using silicon, from the viewpoint of texture.

The portions 24c of the barrier sheets 24 located on the laterally central sides extend over the top sheet 22, and elongated elastic members 24G are longitudinally fixed in a stretched state to ends of lateral center of the portions 24c, with a hot-melt adhesive or the like. The elongated elastic members 24G may use a general material such as styrene rubber, olefin rubber, urethane rubber, ester rubber, polyurethane, polyethylene, polystyrene, styrene-butadiene, silicon, polyester, or the like, formed in a thread, string, or belt shape.

Figure 9:
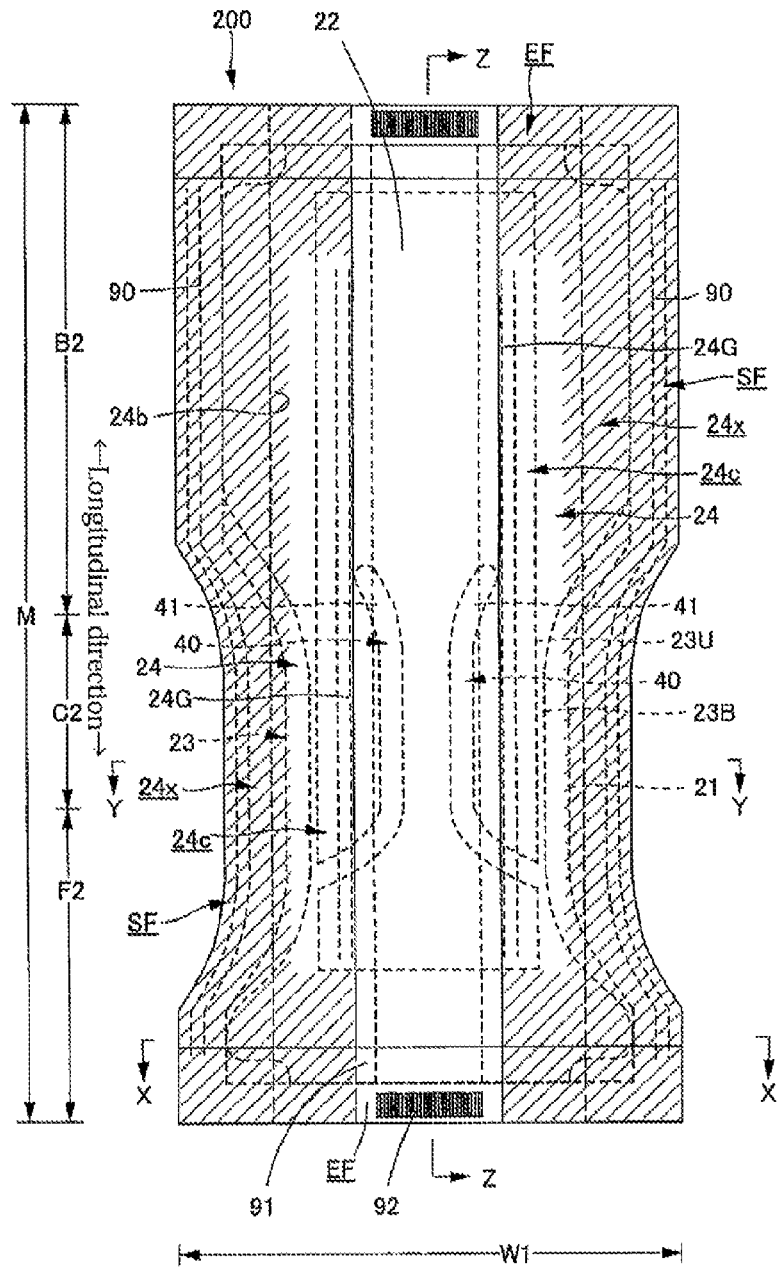
FIG. 9 is a planar view of an internal surface side of an absorbent pad in an open state.
Figure 10:
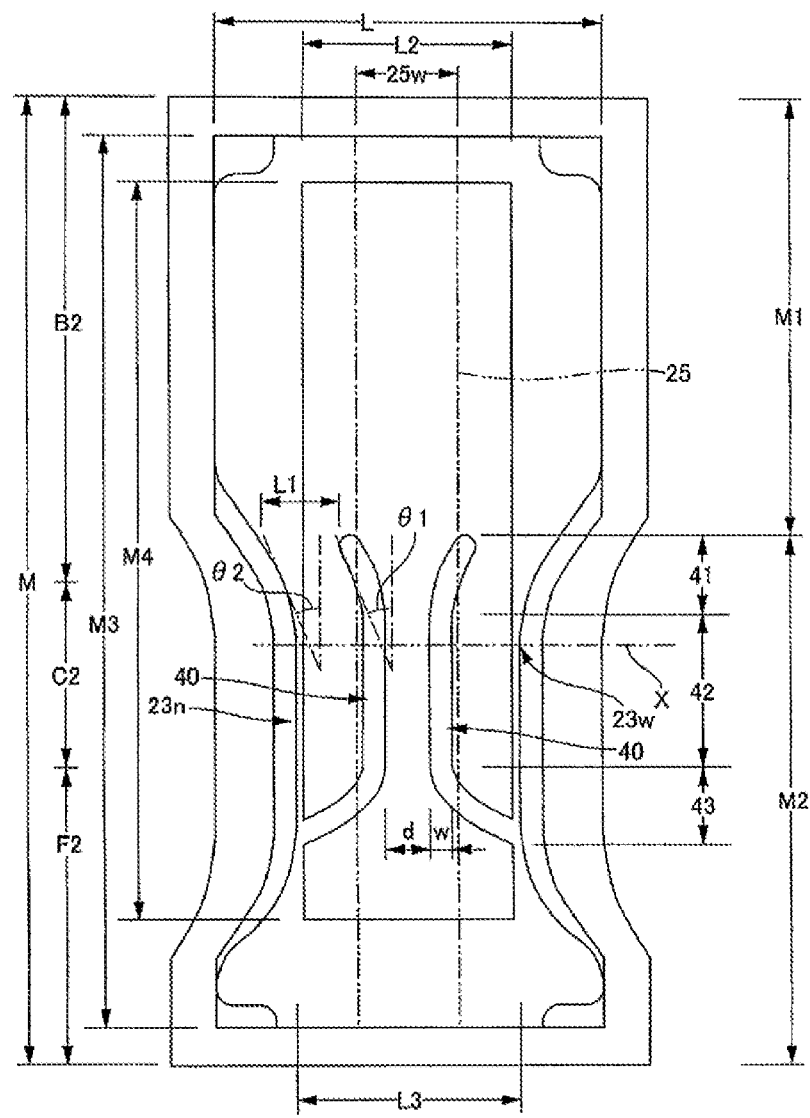
FIG. 10 is a planar view of major components of the absorbent pad.
Figure 11:
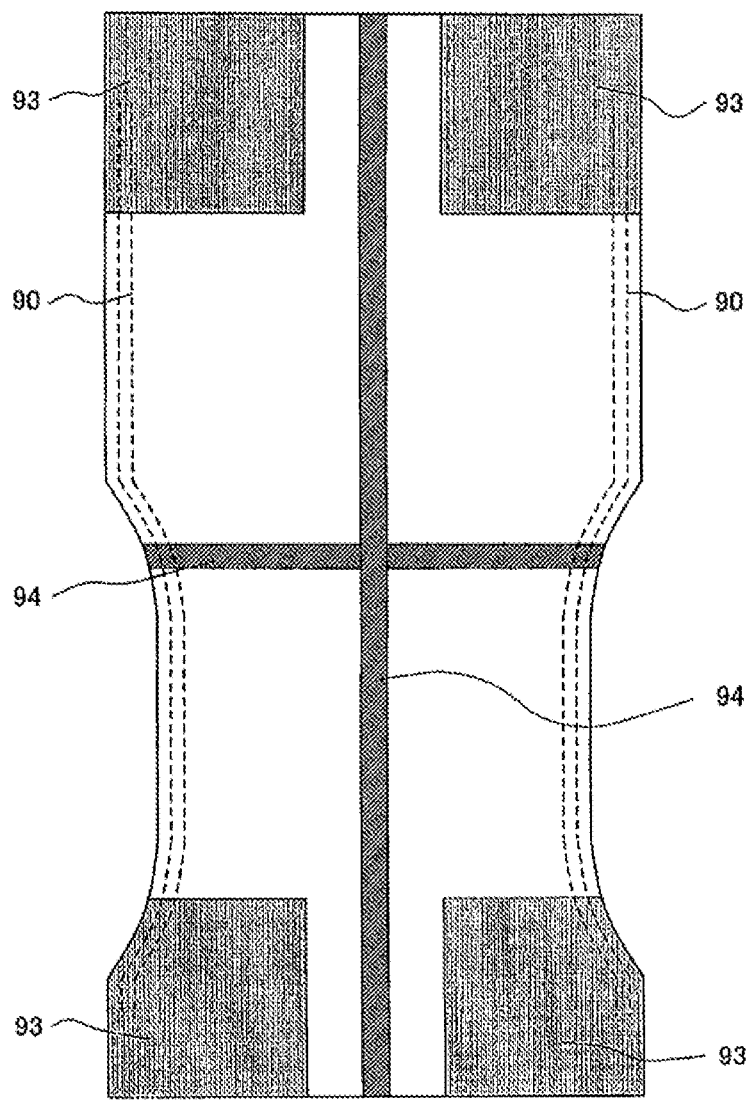
FIG. 11 is a planar view of an external surface side of the absorbent pad in an open state.
Figure 12:
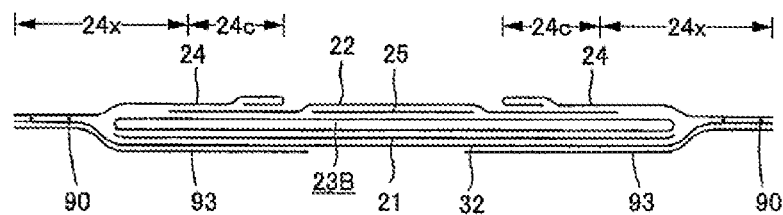
FIG. 12 is a cross section view of FIG. 9 taken along line X-X.
Figure 13:
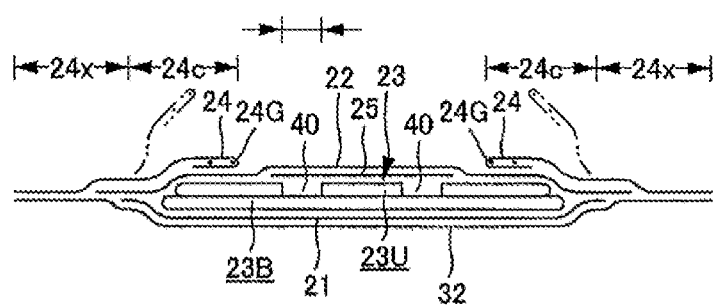
FIG. 13 is a cross section view of FIG. 9 taken along line Y-Y.
Figure 14:
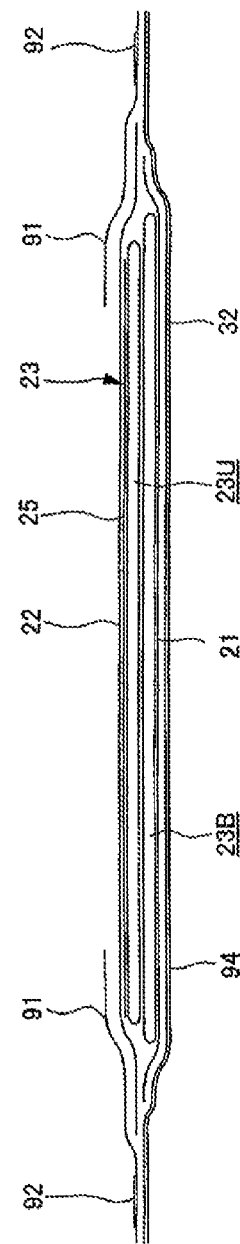
FIG. 14 is a cross section view of FIG. 9 taken along line Z-Z.
Figure 15:
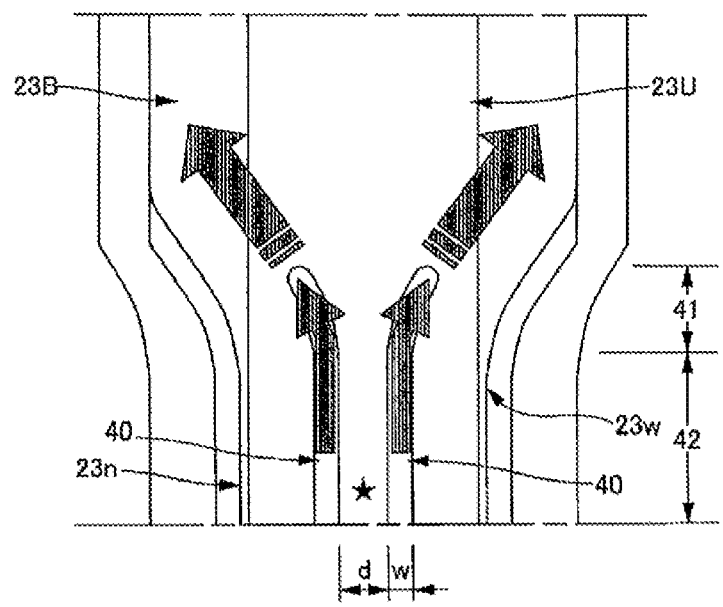
FIG. 15 is a planar view of major components shown in FIG. 10.
Figure 16:
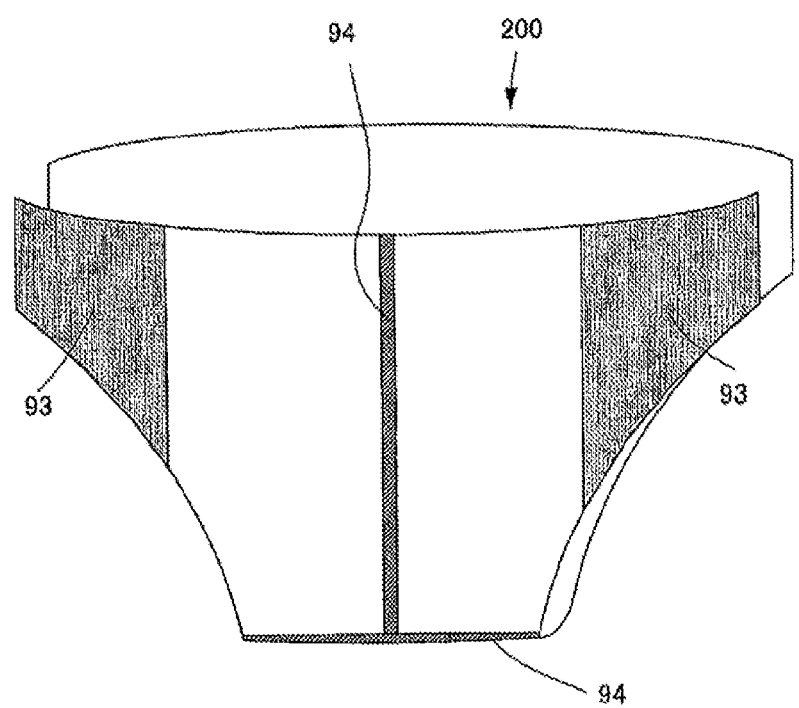
FIG. 16 is a perspective view of the absorbent pad.

The two barrier sheets 24 and 24 are entirely adhered and fixed at the laterally outside portions 24x in a longitudinal direction to the internal surface of the article (in the illustrated mode, the face of the top sheet 22 and the internal surface of the outer sheet 32). In addition, the portions 24c on the laterally central sides are adhered and fixed at the both longitudinal end portions to the internal surface of the article (in the illustrated mode, the face of the top sheet 22), and are not fixed at portions between the both longitudinal end portions to the internal surface of the article (in the illustrated mode, the face of the top sheet 22). The non-fixed portions constitute standing barrier portions with respect to the internal surface of the article (in the illustrated mode, the face of the top sheet 22), as shown in FIG. 9. The non-fixed portions have standing base ends 24b positioned at boundaries between the laterally outside fixed portions 24x and the inside portions 24c of the barrier sheets 24.

The absorbent body 23 may use a base material of an accumulated body of pulp fibers, an aggregate of filaments of cellulose acetate or the like, or a nonwoven fabric, into which high-absorbent polymer particles or the like are mixed or fixed or the like as necessary. If the high-absorbent polymer particles are mixed or the like, the absorbent body 23 may be wrapped with a package sheet (not shown) of crape paper or the like as necessary. In addition, the absorbent body 23 may be formed in a belt shape relatively wider at the ventral side than the back side, or any other appropriate shape such as a rectangle or a trapezoid, or the like.

The absorbent body 23 has a two-layer structure in which the upper layer absorbent body 23U is layered on the lower layer absorbent body 23B so as to have a width L2 smaller than a width L of the lower layer absorbent body 23B and extend longitudinally at least from the crotch portion C2 to the back-side portion B2. A longitudinal length M4 of the upper layer absorbent body 23U may be the same as the longitudinal length M3 of the lower layer absorbent body 23B, but is desirably about 70 to 85% of the length M3. In addition, an entire width L2 of the upper layer absorbent body 23U is desirably about 40 to 60% of the entire width L of the lower layer absorbent body 23B.

Basis weights of fiber and high-absorbent polymer of the absorbent body 23 can be decided as appropriate, but the basis weight of fiber is preferably about 100 to 600 $g/m^2$, and the basis weight of absorbent polymer is preferably about 0 to 400 $g/m^2$. More specifically, the basis weight of fiber of the lower layer absorbent body 23B may be about 80 to 400 $g/m^2$, for example, and the basis weight of high-absorbent polymer of the same may be about 50 to 400 $g/m^2$, for example, the basis weight of fiber of the upper layer absorbent body 23U may be about 80 to 300 $g/m^2$, for example, and the basis weight of high-absorbent polymer of the same may be about 10 to 200 $g/m^2$, for example.

The lower layer absorbent body 23B has a predetermined longitudinally intermediate portion including the crotch portion C2 as a narrowed portion 23n. A minimum width L3 of the narrowed portion 23n is preferably about 50 to 65% of a width L1 of non-narrowed portions on the sides of the narrowed portion 23n in the longitudinal direction thereof. In addition, if it is assumed that the front end of the article is located at a position of 0% and the back end of the article is located at a position of 100%, a front end of the narrowed portion 23n is preferably positioned within a range of 10 to 25%, a back end of the narrowed portion 23n is preferably positioned within a range of 40 to 65%, and a section of the narrowed portion 23n with the minimum width L3 (minimum width section) is preferably positioned within a range of 25 to 30%. In addition, the lower layer absorbent body 23B has no slit at least at positions overlapping upper layer slits 40 described later, and the lower layer absorbent body 23B may have slits at positions other than the overlapping positions, but desirably has no slit in the entire body.

The upper layer absorbent body 23U has on the right and left sides of a laterally central line the upper layer slits 40 penetrating the top and underside surfaces so as to extend from the crotch portion C2 to the back-side portion B2. On the side located more backward than a back-side width increase starting position (minimum width section) 23w at which the width starts to increase in the narrowed portion 23n of the lower layer absorbent body 23B with increasing proximity to the back side, the upper layer slits 40 extends so as to be positioned more laterally outside with increasing proximity to the back side or have diffusion facilitating portions 41 laterally extending from the laterally central side to the lateral outside. The diffusion facilitating portions 41 are preferably formed in a curved shape such as an arc along the narrowed portion 23n of the lower layer absorbent body 23B as in the illustrated example, or may be formed in a straight shape. In addition, the upper layer absorbent body 23U in the illustrated mode is shaped in a rectangle, but may have a narrowed portion (not shown) at a vertically intermediate position as with the lower layer absorbent body.

With such a structure, even if a compressive force is applied to the article in the direction of thickness as when a wearer is in seated position, the upper layer slits 40 provide paths for diffusion of urine. Accordingly, as shown by arrows in FIG. 15, when urine having locally reached the absorbent body 23 at an excretion position (with a solid star mark in FIG. 15) of the crotch portion C2 is diffused to the back side along the upper layer slits 40, the urine is also diffused to the laterally outside along the diffusion facilitating portions 41 of the upper layer slits 40, whereby the urine can be diffused and supplied to a laterally wide area of the wider lower layer absorbent body 23B. This makes it less prone to cause a backflow of urine. In addition, the presence of the upper layer slits 40 at the crotch portion C2 provides a favorable fit of the crotch portion C2 of the article to the body of a wearer.

From the foregoing viewpoint, front ends of the diffusion facilitating portions 41 of the upper layer slits 40 are preferably positioned on a lateral line passing through the back-side width increase starting position 23w at the narrowed portion 23n of the lower layer absorbent body 23B or in the vicinity of the lateral line. In addition, if it is assumed that an angle formed by a tangent line to a laterally outside edge of the diffusion facilitating portion 41 of the upper layer slit 40 with respect to the longitudinal direction is designated as $\theta 1$ and an angle formed by a tangent line to a side edge of the narrowed portion 23n of the lower layer absorbent body 23B with respect to the longitudinal direction is designated as $\theta 2$, the following relational expressions are preferably satisfied at longitudinal positions within the longitudinal zone corresponding to the diffusion facilitating portions 41 of the upper layer slits 40:

$$0° \leq \theta 1 \leq 90°$$

$$\theta 1 - 20° \leq \theta 2 \leq \theta 1 + 20°$$

In particular, the following relational expressions are preferably satisfied:

$$0° \leq \theta 1 < 40°$$

$$\theta 1 - 10° \leq \theta 2 \leq \theta 1 + 5°.$$

Further, back ends of the diffusion facilitating portions 41 of the upper layer slits 40 are preferably separated from side edges of the lower layer absorbent body 23B. In this case, if it is assumed that a width of the back end of the narrowed portion 23n of the lower layer absorbent body 23B is designated as L, a lateral separation distance L1 is preferably configured to satisfy the relationship 10 mm$\leq$L1$\leq$L/3, in particular satisfy the relationship 50 mm$\leq$L1$\leq$L/3. As in the foregoing, when the back ends of the diffusion facilitating portions 41 of the upper layer slits 40 are sufficiently extended to the side portions of the lower layer absorbent body 23B while being separated to some extent from the side edges of the lower layer absorbent body 23B, it is possible to diffuse urine in a sufficiently wide area of the lower layer absorbent body 23B, without excessive diffusion of urine in the lateral direction due to the presence of the upper layer slits 40.

If it is assumed that the entire length of the absorbent pad 200 is designated as M, a longitudinal length of the back-side portion B2 of the absorbent pad 200 located on the back side of the back ends of the diffusion facilitating portions of the upper layer slits 40 is designated as M1, and a longitudinal length of the ventral-side portion of the absorbent pad 200 located on the ventral side of the back ends of the diffusion facilitating portions 41 of the upper layer slits 40 is designated as M2, the absorbent pad 200 is preferably configured to satisfy the relationship M/2$\leq$M2<M, in particular satisfy the relationship M/7$\leq$M2<M/3. As in the foregoing, when the back ends of the diffusion facilitating portions 41 of the upper layer slits 40 are sufficiently extended to the back side while being sufficiently separated from the back end of the article, it is possible to diffuse appropriately urine to the back side by the upper layer slits 40. If the upper slits 40 are excessively extended to the back side of the article, urine is excessively diffused to the back side with a possibility of causing so-called back-side leakage.

The width w of the upper layer slits 40 can be decided as appropriate, but preferably in general falls within a range of 10 to 30 mm, in particular a range of 10 to 15 mm. If the width w of the upper layer slits 40 is too small, the slits are prone to be crushed in the lateral direction. If the width w of the upper layer slits 40 is too small, the upper and lower members (for example, a package sheet for the absorbent body 23) enter into the slits 40. Either case is not preferred because of decrease in space for diffusion.

Meanwhile, the upper layer slits 40 preferably have introduction portions 42 with a right-left slit interval d of 20 to 40 mm therebetween as portions continuous with the ventral sides of the diffusion facilitating portions 41. The more preferred interval d is 10 to 40 mm. A longitudinal length of the introduction portions 42 is preferably about 10 to 35% of the entire length of the article, in particular about 12 to 35% of the same.

Further, the upper layer slits 40 have ventral-side interval increased portions 43 that extend toward the side edges of the upper layer absorbent body 23U with a change in orientation from the front ends of the introduction portions 42 to the lateral outside. The ventral-side interval increased portions 43 preferably extend so as to be positioned laterally outward with increasing proximity to the ventral side, or extend laterally in a curved or straight shape from the laterally central side to the lateral outside. In addition, the ventral-side interval increased portions 43 preferably have leading ends passing through the side edges of the upper layer absorbent body 23U as in the illustrated mode. Alternatively, the leading ends may not reach the side edges of the upper layer absorbent body 23U but be separated from the side edges.

To enhance a fit of the crotch portion C2, leg-around resilient members 90 are arranged at the side flaps SF on the both lateral sides of the absorbent pad 200 so as to extend from the engagement members 93 of the ventral-side portion F2 to the engagement members 93 of the back-side portion B2 of the outer sheet 32.

<Absorbent Article>

Figure 17:
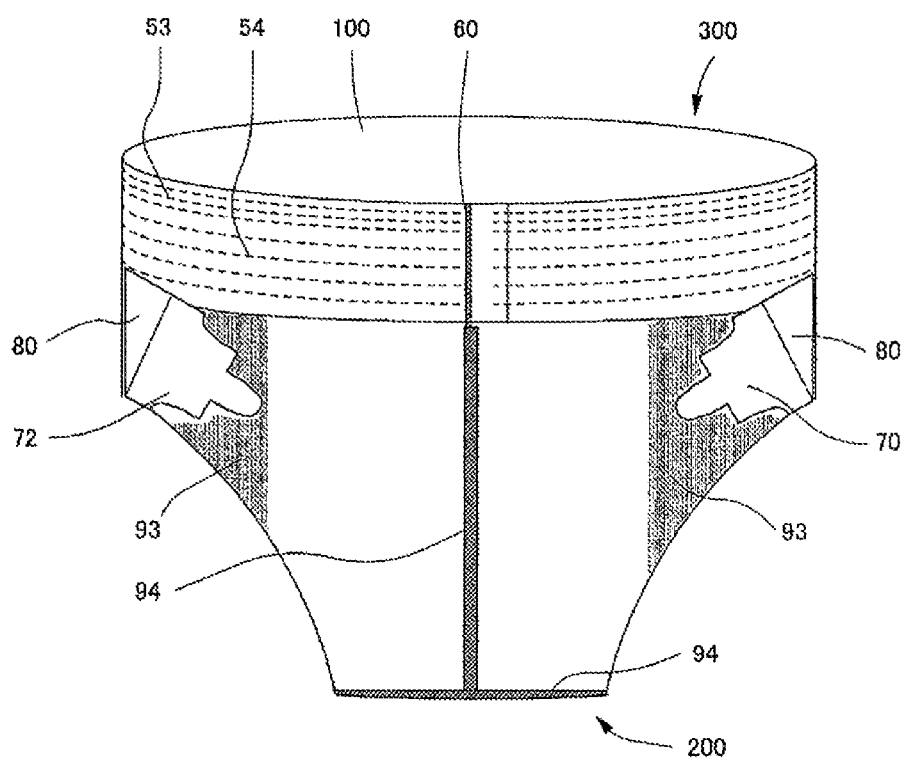
FIG. 17 is a front (ventral-side) perspective view of the absorbent pad attached to the waist band.
Figure 18:
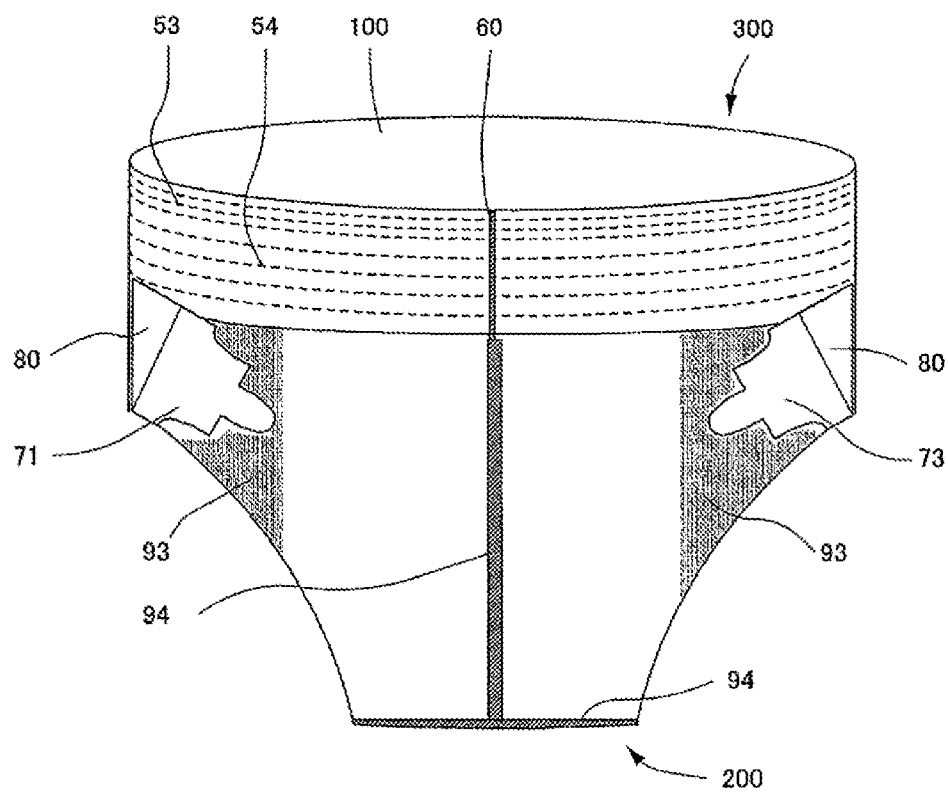
FIG. 18 is a back (back-side) perspective view of the absorbent pad attached to the waist band.

As shown in FIGS. 17 and 18, an absorbent article 300 includes the waist band 100 and the absorbent pad 200. The absorbent article 300 can be formed by engaging and attaching the engagement members 93 of the ventral-side portion F2 of the absorbent pad 200 to the hook materials 84 of the first and second ventral-side engagement portions 70 and 72 of the waist band 100, and then engaging and attaching the engagement members 93 of the back-side portion B2 of the absorbent pad 200 to the hook materials 84 of the first and second back-side engagement portions 71 and 73 of the waist band 100.

If the absorbent article 300 is attached by a nursing care assistant to a wearer from the back side, first, the engagement members 93 of the back-side portion B2 of the absorbent pad 200 are engaged and attached to the hook materials 84 of the first and second back-side engagement portions 71 and 73 of the waist band 100, and the central portion of the belt-shaped body 50 of the waist band 100 is applied to the back side of the wearer, and the waist of the wearer is surrounded with the belt-shaped body 50 while the both peripheral ends of the belt-shaped body 50 are stretched to the right and left sides of the waist of the wearer, and the hook material 56 and the loop material 57 of the belt-shaped body 50 are engaged at the ventral side of the wearer to shape the belt-shaped body 50 in a circle, and then the engagement members 93 of the ventral-side portion F2 of the absorbent pad 200 are engaged with the hook materials 84 of the first and second ventral-side engagement portions 70 and 72 of the waist band 100, thereby to attach the absorbent article 300 to the wearer. At that time, the absorbent article 300 can be easily attached to the wearer by aligning the marks 60 of the waist band 100 and the marks 94 of the absorbent pad 200 as described above.

In addition, before engaging and attaching the engagement members 93 of the back-side portion B2 of the absorbent pad 200 to the hook materials 84 of the first and second back-side engagement portions 71 and 73 of the waist band 100, the above-described temporary fastening members 92 of the absorbent pad 200 are temporarily fastened to the belt-shaped body 50 of the waist band 100, which allows a nursing care assistant to use freely his/her both hands. This makes it possible to attach the absorbent article 300 to the wearer in a further easier manner.

INDUSTRIAL APPLICABILITY

The present invention can be used for absorbent pads and absorbent articles.

BRIEF DESCRIPTION OF NUMERALS

21 Liquid impervious back sheet
22 Liquid pervious top sheet
23U Upper layer absorbent body
23B Lower layer absorbent body
24 Barrier sheet
32 Outer sheet
40 Upper layer slit
50 Belt-shaped body
51 Upper layer nonwoven fabric
52 Lower layer nonwoven fabric
53 Waist resilient member
54 Lower waist resilient member
55 Supporting member
56 Hook material
57 Loop material
60 Mark
61 First cut-off portion
62 Second cut-off portion
70 First ventral-side engagement portion
71 First back-side engagement portion
72 Second ventral-side engagement portion
73 Second back-side engagement portion
74 Fixed portion
80 Attachment sheet
81 Resilient sheet
82 Upper layer nonwoven fabric
83 Lower layer nonwoven fabric
84 Hook material
85 Resilient member
90 Leg-around resilient member
91 Leakage prevention sheet
92 Temporary fastening member
93 Engagement member
94 Mark
100 Waist band
200 Absorbent pad
300 Absorbent article
FIG. 9
(1) Lateral direction
(2) Longitudinal direction

The invention claimed is:

1. An absorbent article having an absorbent pad and a waist band across which the absorbent pad is attached, wherein
the absorbent pad includes: a liquid pervious top sheet; a liquid impervious back sheet; an absorbent body extending longitudinally between the liquid pervious top sheet and the liquid impervious back sheet at least from a crotch portion to a back-side portion; and an outer sheet on an external surface of the liquid impervious back sheet, and wherein
engagement members with indications of attachment positions are arranged at both corners of a ventral-side portion and a back-side portion on an external surface of the outer sheet,
the waist band includes:
a belt-shaped body having a belt-shaped nonwoven fabric and resilient members arranged in a stretched state along a periphery of the nonwoven fabric;
a hook material of a mechanical fastener that is attached to one peripheral end portion of the belt-shaped body, and an engagement portion that is attached to the other peripheral end of the belt-shaped body and is capable of engaging with the hook material;
a first ventral-side engagement portion across which the engagement members at the ventral-side portion of the absorbent pad are engaged, and a first back-side engagement portion across which the engagement members at the back-side portion of the absorbent pad are engaged, at a portion of the belt-shaped body opposed to the right iliac bone of a wearer;
a second ventral-side engagement portion across which the engagement members at the ventral-side portion of the absorbent pad are engaged, and a second back-side engagement portion across which the engagement members at the back-side portion of the absorbent pad are engaged, at a portion of the belt-shaped body opposed to the left iliac bone of a wearer, and wherein
hook materials of mechanical fasteners capable of engaging with the engagement members of the absorbent pad are attached to internal surfaces of the first and second ventral-side engagement portions and the first and second back-side engagement portions, and
the first and second ventral-side engagement portions and the first and second back-side engagement portions are inclined with respect to the longitudinal direction of the belt-shaped body, and extend beyond a lower waist portion opening edge of the belt-shaped body.

2. The absorbent pad according to claim 1, wherein
leg-around resilient members are arranged at side flap portions of the absorbent pad, and
the leg-around resilient members extend longitudinally from the crotch portion to positions opposed to the engagement members at the ventral-side portion and the back-side portion of the outer sheet.

3. The absorbent article according to claim 2, wherein temporary fastening members are arranged at end flap portions of the absorbent pad.

4. The absorbent article according to claim 1, wherein
fixed portions of the first and second ventral-side engagement portions with the belt-shaped body are formed at a position opposed to the iliac bone of a wearer, and
a shape of the fixed portions is approximate to a substantially triangular shape of the iliac bone.

5. The absorbent article according to claim 1, wherein
an end of the first ventral-side engagement portion and an end of the second back-side engagement portion are fixed with a clockwise inclination of 30 to 60 degrees with respect to the periphery of the belt-shaped body, and
an end of the second ventral-side engagement portion and an end of the first back-side engagement portion are fixed with a counterclockwise inclination of 30 to 60 degrees with respect to the periphery of the belt-shaped body.

6. The absorbent article according claim 1, wherein
when being stretched by 150%, a stretching stress of the resilient members arranged at the waist portion of the belt-shaped body is 10 to 35 g, and a stretching stress of the resilient members arranged at the lower waist portion of the belt-shaped body is 4 to 15 g.

7. The absorbent article according to claim 1, wherein
recognizable marks are provided on an external surface of an end portion and an external surface of a peripherally central portion of the belt-shaped body, such that the ventral-side central portion and the back-side central portion have the marks when the belt-shaped body is shaped in a circle, and a longitudinally extending recognizable mark is provided at the laterally central portion of the outer sheet of the absorbent pad.

8. The absorbent article according to claim 1, wherein
first cut-off portions are formed from end pieces of the lower waist portion at both end portions of the belt-shaped body,
a second cut-off portion is formed from an end piece of the lower waist portion at an peripherally central portion of the belt-shaped body, and
when the belt-shaped body is shaped in a circle, the belt-shaped body has a ventral-side cut-off portion including the pair of first cut-off portions and a ventral-side cut-off portion including the second cut-off portion.

9. The absorbent article according to claim 1, wherein
a first skin protection portion is provided on the internal surface of the belt-shaped body opposed to the right iliac bone of a wearer, and
a second skin protection portion is provided on the internal surface of the belt-shaped body opposed to the left iliac bone of a wearer.

\* \* \* \* \*